United States Patent
Memmolo et al.

(10) Patent No.: US 9,314,319 B2
(45) Date of Patent: Apr. 19, 2016

(54) TRANSFER PART FOR AN IMPLANT

(75) Inventors: Marcello Memmolo, Sissach (CH);
Daniel Günter, Waldenburg (CH)

(73) Assignee: Straumann Holding AG, Bassel (CH)

( * ) Notice: Subject to any disclaimer, the term of this patent is extended or adjusted under 35 U.S.C. 154(b) by 864 days.

(21) Appl. No.: 10/575,988

(22) PCT Filed: Oct. 15, 2004

(86) PCT No.: PCT/EP2004/011671
§ 371 (c)(1),
(2), (4) Date: Apr. 17, 2006

(87) PCT Pub. No.: WO2005/037126
PCT Pub. Date: Apr. 28, 2005

(65) Prior Publication Data
US 2007/0072148 A1 Mar. 29, 2007

(30) Foreign Application Priority Data
Oct. 16, 2003 (EP) .................................... 03023621

(51) Int. Cl.
*A61C 8/00* (2006.01)
(52) U.S. Cl.
CPC ............. *A61C 8/0087* (2013.01); *A61C 8/0089* (2013.01)
(58) Field of Classification Search
CPC .......................... A61C 8/0089; A61C 8/0087
USPC .............. 433/172–174, 201.1, 141; 206/63.5, 206/368, 369
See application file for complete search history.

(56) References Cited

U.S. PATENT DOCUMENTS

| 5,078,605 A * | 1/1992 | Sutter et al. .................... 433/165 |
| 5,947,733 A * | 9/1999 | Sutter et al. .................... 433/173 |
| 6,206,696 B1 * | 3/2001 | Day .............................. 433/141 |
| 6,247,932 B1 * | 6/2001 | Sutter .......................... 433/173 |
| 6,261,097 B1 | 7/2001 | Schmutz |
| 6,663,388 B1 * | 12/2003 | Schar et al. .................... 433/173 |
| 2004/0096804 A1 * | 5/2004 | Vogt et al. .................... 433/173 |
| 2004/0101808 A1 * | 5/2004 | Porter et al. .................. 433/173 |

FOREIGN PATENT DOCUMENTS

| WO | WO 97/06930 | 2/1997 |
| WO | WO 00/02496 | 1/2000 |
| WO | WO 01/50978 A1 | 7/2001 |
| WO | WO 02/087461 A1 | 11/2002 |

* cited by examiner

*Primary Examiner* — Ralph Lewis
(74) *Attorney, Agent, or Firm* — Scully Scott Murphy and Presser

(57) ABSTRACT

A transfer part for holding an implant has a clamping portion for clamping connection with the implant. The clamping portion has a radial groove, a clamping ring and a force transmission element. The clamping ring is insertable into the radial groove to directly engage with the implant. The force transmission element secures the clamping connection against rotation. An inner ampule for receiving and securing a transfer part for holding an implant has an upper fixing portion and a lower fixing portion. The upper fixing portion reaches to a large surface recess in the ampule for insertion and removal of the transfer part, and has a laterally open indentation enlarging towards the recess adapted for the closely fitting insertion of the transfer part. The lower fixing portion has a laterally open indentation towards the recess adapted to receive the implant.

10 Claims, 4 Drawing Sheets

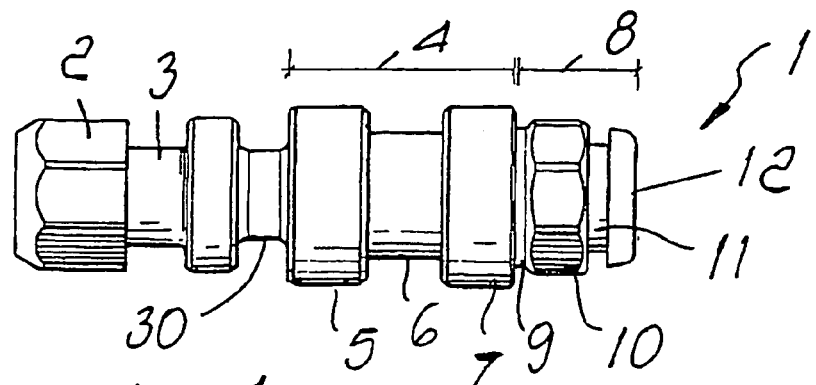
Fig. 1
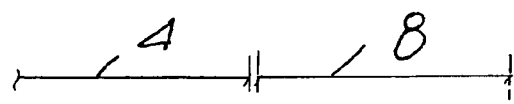
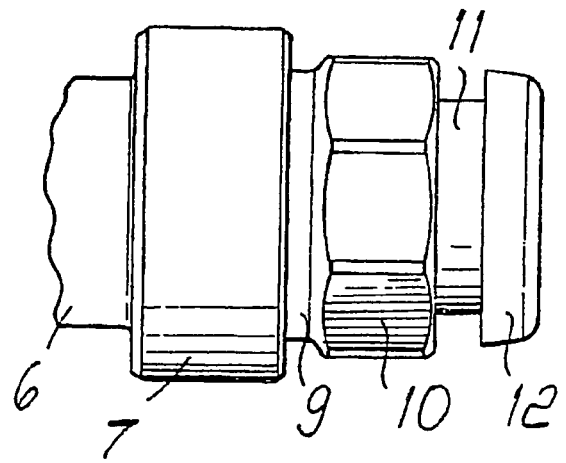
Fig. 1A
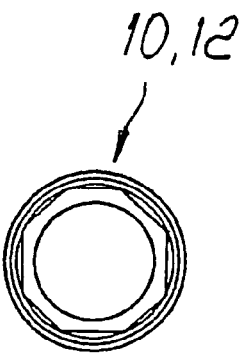
Fig. 1B
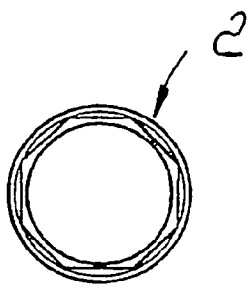
Fig. 1C

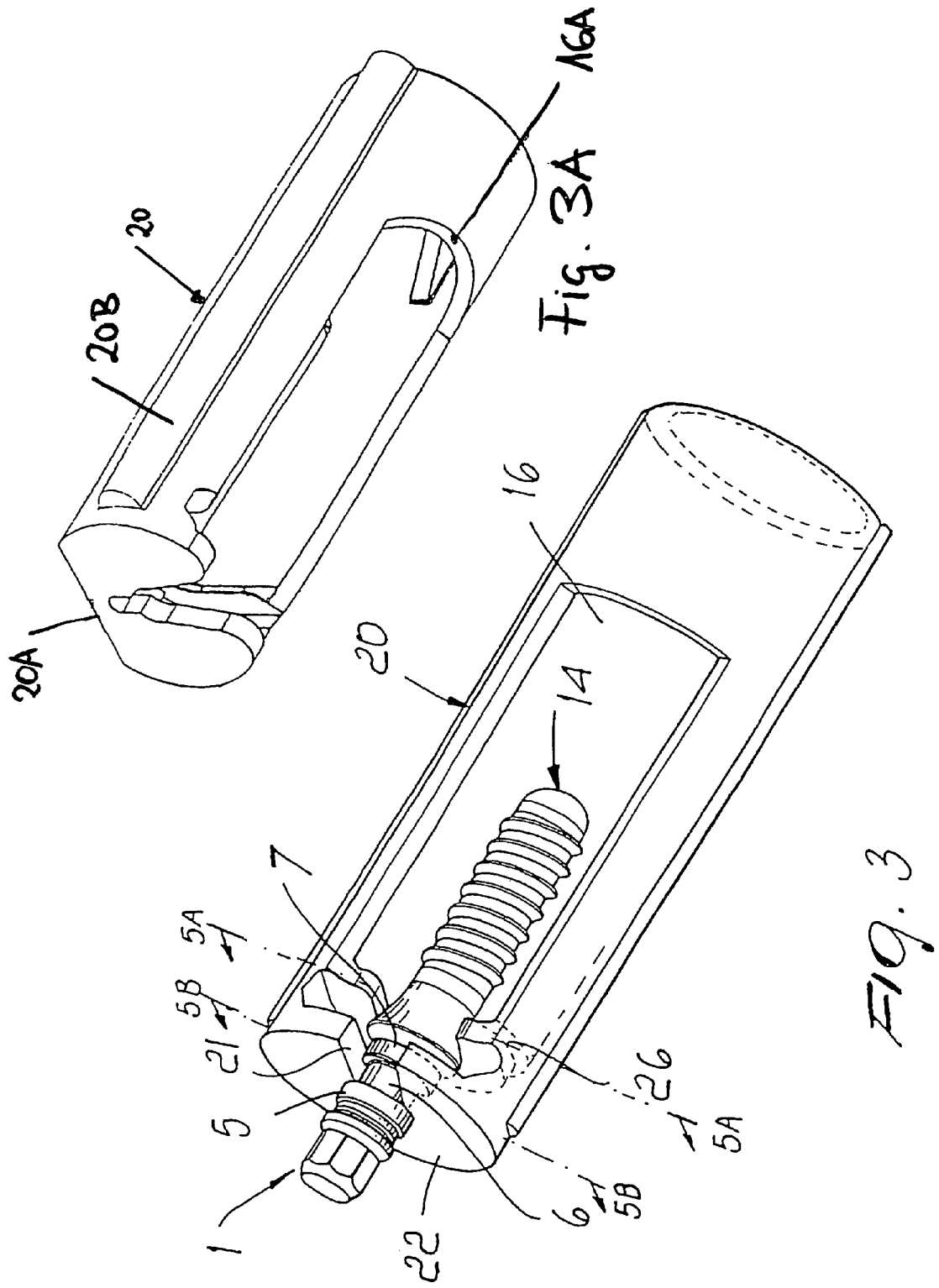

TRANSFER PART FOR AN IMPLANT

The present invention refers generally to an improved transfer part or holding element for an implant and specifically to an improved transfer part or holding element for an implant which is suitable to secure over a longer period of time the implant in an inner ampule filled with liquid.

PRIOR ART

From WO-A1-98 55039 (which corresponds to U.S. Pat. No. B1-6,261,097), a rotationally symmetrical holding element for an implant, particularly a dental implant, to be placed in a bone, and an inner ampule or ampule for storing the implant are known, wherein the holding element can be brought threadingly into engagement with the implant by means of a screw shank. The unit, which consists of the holding element and the implant screwed into it, can be inserted in an inner ampule for storage and for transport of the implant, which has a fixing portion into which the holding element can be inserted directly or indirectly, and a lateral recess corresponding to the length of the unit through which the implant with the holding element can be removed. The holding element of the prior art has, at the end opposite to the screw shank, an extension with an external polyhedron (particularly an octagon), to which a tool, e. g. a rotary tool, can be applied. A securing element, preferably an O-ring, is provided in a radial groove below the extension. In addition, according to WO-A1-98 55039, an exterior capsule with a cover to be screwed thereon is configured in such a way that the holding element with the implant can be locked into place axially between the bottom of the exterior capsule and the cover. The entire content of WO-A1-98 55039 is hereby incorporated by reference.

U.S. Pat. No. B1-6,247,932 describes a container for a dental implant wherein the transfer part is engagingly connected with the implant. The known container is configured analogously to the outer capsule of WO-A1-98 55039 for receiving and securing the transfer part with the implant snappingly attached thereto. Additionally, U.S. Pat. No. B1-6,247,932 provides means for securing the implant against rotation with regard to the transfer part or means for the transmission of forces from the transfer part to the implant, respectively.

A transfer part with a snap-on mechanism is known from U.S. Pat. No. B1-6,206,696, where attachment to the implant takes place by means of snapping into a healing screw. Similar transfer parts are known from WO-A1-00 02496 and WO-A1-01 50978, which can be attached to a healing screw fastened to the implant by means of a snap-in process.

SUMMARY OF THE INVENTION

In view of the prior art described above, an object of the present invention is the provision of a transfer part or holding element for an implant, in particular for a dental implant, which features both a secure and an easily established connection with an implant.

In the framework of the above object, a special task of the present invention is the provision of a transfer part or holding element for an implant, in particular for a dental implant, which maintains the secure connection with the implant in a liquid medium, e. g. in a sterile storage liquid for a dental implant.

This and other tasks to be found in the following description are solved by a transfer part for a dental implant according to the attached claims.

Other features and advantages of the present invention as well as the functioning of different embodiments of the present invention are described below with reference to the accompanying figures. These figures illustrate the present invention and, in combination with the specification, serve to explain the basics of the invention and to enable a person skilled in the art to manufacture and use the invention. In this connection:

FIG. 1 shows a view of a transfer part according to an embodiment of the present invention;

FIG. 1A shows an enlarged view of a portion of the transfer part in FIG. 1, wherein a radial groove for receiving a clamp ring according to the invention is formed;

FIG. 1B shows a right lateral view of the transfer part in FIG. 1;

FIG. 1C shows a left lateral view of the transfer part in FIG. 1;

FIG. 3 shows a perspective view of the transfer part in FIG. 2 with the dental implant placed on it and the inner ampule for storage and transport of the implant;

FIG. 3A shows a modified embodiment of the inner ampule in FIG. 3;

DESCRIPTION OF THE PREFERRED EMBODIMENTS OF THE INVENTION

Figure 2:
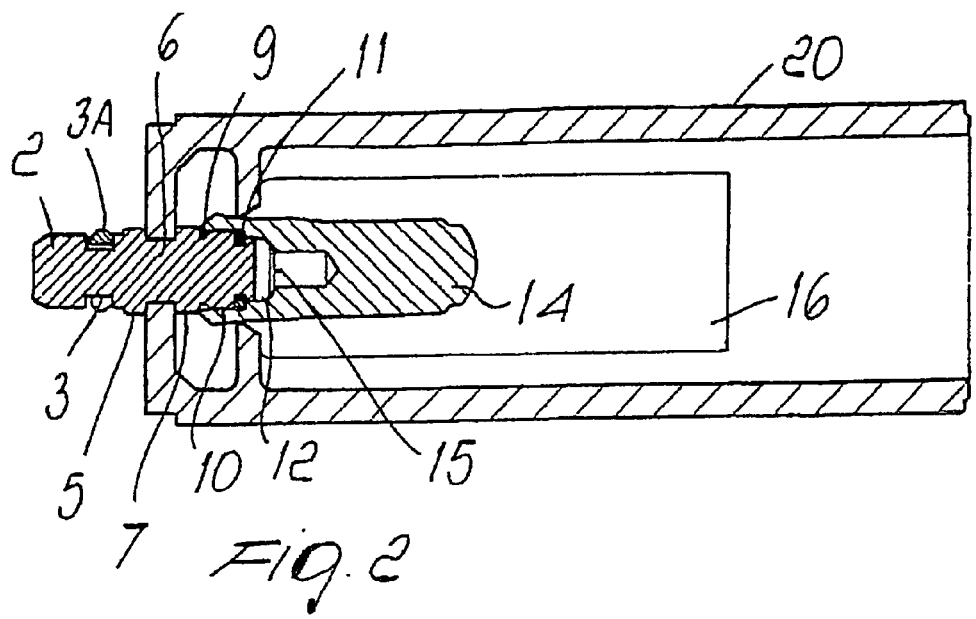
FIG. 2 shows a sectional view of a schematic transfer part according to FIG. 1 with a dental implant placed on it and an inner ampule for storage and transport of the implant.
Figure 2A:
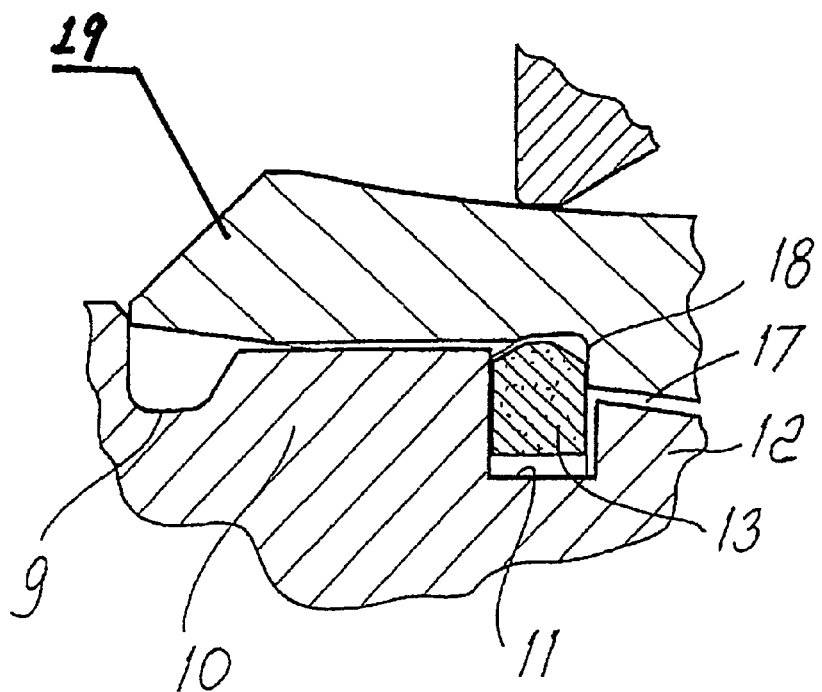
FIG. 2A shows an enlarged view of a portion of the transfer part and the implant in FIG. 1A, wherein a radial groove for receiving a clamp ring according to the invention is formed.
Figure 4:
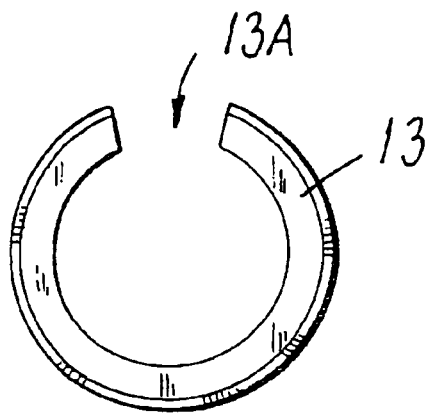
FIG. 4 shows a top view of the clamp ring of the transfer part according to the invention in FIG. 1.
Figure 4A:
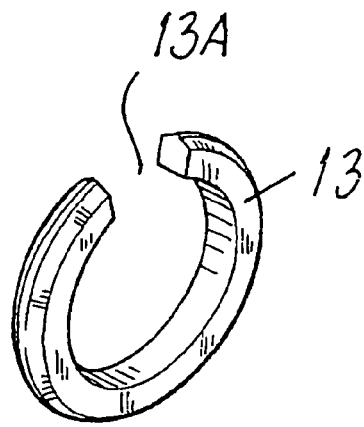
FIG. 4A shows a perspective view of the clamp ring of the transfer part according to the invention in FIG. 1.

With reference to FIGS. 1 to 2A, a currently preferred embodiment of a rotationally symmetrical transfer part or holding element according to the present invention is described wherein the transfer part is generally designated by the reference number 1.

In analogy to WO-A1-98 55039, the transfer part 1 has a free extension 2 which ends at the top, with an outer polyhedron (preferably an octagon) and an adjacent first radial groove 3 for placing therein a securing element, preferably an O-ring 3A shown in FIG. 2. A rotational tool or an adaptor (not shown) for a rotational tool or the like can be directly applied at the free extension 2; by means of this, the implant can be removed from an inner ampule without being touched. The inner ampule can be inserted in conventional outer capsule.

In addition, the transfer part 1, analogously to WO-A1-98 55039, has a fixing portion generally designated by the reference number 4 and positioned below the extension 2. The fixing portion 4 which is configured to be received in the inner ampule comprises a first and a second cylindrical collar 5 and 7, respectively, between which a cylinder portion 6, reduced in diameter, is located. Between the extension 2 and the fixing portion 4, a breaking point designated by the reference number 30 is formed.

According to the invention, the transfer part 1 furthermore has a clamping portion designated generally by the reference number 8 and located below the fixing portion 4. The clamping portion 8 comprises a third radial groove 9, a force transmission element 10, a second radial groove 11 and an end 12 in the form of a truncated cone. The force transmission element 10 has an outer polyhedron, preferably an octagon, as a surface, which has a cross section substantially equal to or slightly smaller than the outer polyhedron of the extension 2. in the simplified illustration in FIG. 2, this breaking point 30 is omitted.

According to the invention, the transfer part 1 furthermore has a clamping portion designated generally by the reference number 8 and located below the fixing portion 4. The clamping portion 8 comprises a third radial groove 9, a force transmission element 10, a second radial groove 11 and an end 12 in the form of a truncated cone. The force transmission element 10 has an outer polyhedron, preferably an octagon, as a surface, which has a cross section substantially equal to or slightly smaller than the outer polyhedron of the extension 2. in the simplified illustration in FIG. 2, this breaking point 30 is omitted.

FIG. 2 shows the clamp ring 13 according to the invention in an assembled state with a schematically represented dental implant 14 which can be similar to the dental implant of WO-A1-98 55039. However, it is readily apparent to the person skilled in the art of implantology that the transfer part of the present invention is not limited to the implant shown in WO-A1-98 55039 but that it can be utilized in combination with other conventional implants or other abutments without departing from the scope of the invention as defined in the appended claims.

The dental implant 14 in FIG. 2 has an inner space 15 which is configured with an area 17 (e. g. octagon) which matches the outer polyhedron of the force transmission element 10 so that a rotationally secure and non-positive connection between the transfer part 1 and the dental implant 14 is implemented.

Preferably, the implant undercut 18 designed for subsequent insertion of the dental implant 14 is also dimensioned suitably for clampingly receiving the clamp ring 13. A conical implant shoulder 19 in the upper area of the implant 14 closely surrounds the first ring groove 9 of the transfer part 1.

The dental implant 14 in combination with the transfer part 1 clamped thereon can be inserted in an inner ampule 20 having a large-area recess 16, with the inner ampule 20 being inserted in a closable outer capsule (not shown) for storage and transport of the implant. The recess 16 shown in FIG. 3 has a substantially rectangular shape, although its lower portion 16A, as shown in FIG. 3A, can have a rounded shape, facilitating the handling of the implant 14.

Both the inner ampule 20 and the outer capsule can be implemented according to WO-A1-98 55039, although other embodiments of these elements with the transfer part according to the invention or with the combination of this transfer part with the implant, respectively, can be implemented as well. Naturally, the outer capsule must be closed sealingly if it contains a liquid, e. g. an electrolyte or an aqueous solution for storing the dental implant.

Figure 5A:
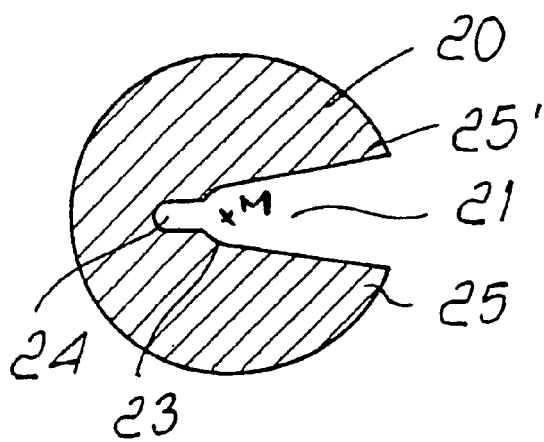
FIG. 5A is a sectional view through a top fixing portion of the ampule according to the present invention.
Figure 5B:
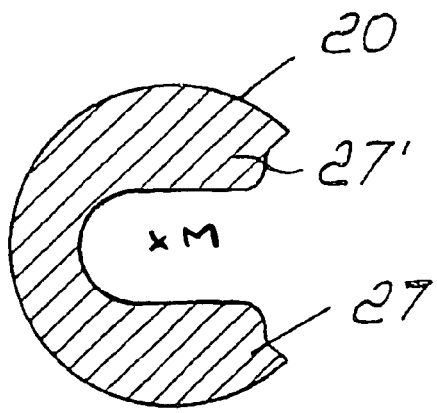
FIG. 5B is a sectional view through a bottom fixing portion of the inner ampule according to the present invention.

Another aspect of the present invention refers to an improved inner ampule 20 with an upper fixing portion 22 reaching to the large surface recess 16. The upper fixing portion 22 is modeled analogously to the fixing portion of WO-A1-98 55039 and has a laterally open trumpet like indentation 21, the latter pointing in the same direction as the large surface recess 16. The indentation 21 can be provided with rounded corners at the peripheral entrance, wherein these rounded corners can also be omitted according to the invention as shown in FIGS. 3 and 5. In the vicinity of the theoretical central axis M of the inner ampule 20, the indentation 21 has a necking 23 behind which the indentation 21 is enlarged in semi-circular shape. In this way, two opposite jaws 25, 25' are formed on the fixing portion 22. Beyond the indentation 21, further cutting into the fixing portion 22 towards the cylinder barrel of the inner ampule, an expansion groove 24 is provided so that when a transfer part 1 or a fixing portion 4 of the transfer part 1, respectively, are pressed in and out between the jaws 25, 25', these can be better straddled elastically. After the necking 23 has passed the cross-section of the transfer part 1 when the latter is pressed in, the transfer part 1 is engaged in the indentation 21, and the jaws 25, 25' become close again.

To better fix the transfer part 1 in the inner ampule 20 and to prevent the transfer part 1 from separating from the implant 14 during transport, a lower fixing portion 26 of the inner ampule 20 is provided which is configured to receive the conical implant shoulder 19. The lower fixing portion 26 of the inner ampule 20 has two support wings 27, 27' extending in alignment with the indentation 21, set back a little from it, so that a close fitting for the implant shoulder 19 is formed. The support wings 27, 27' can also be provided with corresponding rounded corners at the peripheral entrance for better guidance of the implant shoulder 19.

Thus, the conical implant shoulder 19, supported by the support wings 27, 27', is biased or pressed upwards in the direction of the transfer part 1, avoiding other means known from the prior art for securing transport of the dental implant in its lower portion. The support wings according to the invention can be used independently of the features described above, in particular independently of the improved transfer part with the clamp ring, with every appropriately configured combination of implant and transfer part, and represent another aspect of the invention which, as already mentioned, solves the problem of securing transport of the transfer part and/or the implant.

Furthermore, the inner ampule 20, as can be seen in FIGS. 3 and 3A, can be equipped with enlarged anti-rolling ribs 20B for preventing an undesired rolling or turning of the ampule 20. In addition, an orientation surface 20A (see FIG. 3A) can advantageously be provided on the side opposite to the indentation 21.

When technical features mentioned in any of the claims are provided with a reference number, these reference numbers have been included solely to increase intelligibility of the claims. Accordingly, these reference numbers have no limiting effect on the scope of each element which is identified, by way of example, by such reference numbers.

The invention claimed is:

1. A combination of a dental implant and a transfer part for holding the dental implant, the transfer part comprising:
   a free extension at one end of the transfer part for coupling a rotational tool and a first radial groove adjacent to the free extension for receiving a securing element;
   a clamping portion at the other end of the transfer part for the clamping connection of the transfer part to the dental implant, said clamping connection providing the sole connection between the transfer part and the implant, the clamping portion comprising a force transmission element for securing the clamping connection against rotation, a second radial groove directly adjacent to the force transmission element, and a clamp ring insertable into the second radial groove to engage with the dental implant,
   wherein the dental implant comprises an internal undercut positioned correspondingly to the second radial groove of the clamping portion of the transfer part and dimensioned suitably to provide together with the second radial groove a receiving means for clampingly receiving the clamp ring.

2. The combination according to claim 1, with the clamp ring being formed from polyether ether ketone (PEEK) so that a secure clamping connection in a liquid is provided.

3. The combination according to claim 1, with the force transmission element having an octagonal surface.

4. The combination according to claim 1, with the clamp ring in its non-assembled state having a gap at its outer circumference.

5. The combination according to claim 1, further comprising an extension having an outer polyhedron and a fixing portion to be received in an inner ampule, with the fixing portion positioned between the extension and the clamping portion.

6. A combination of an inner ampule and a transfer part for a dental implant,
- wherein the transfer part comprises: a free extension at one end of the transfer part for coupling a rotational tool and a first radial groove adjacent to the free extension for receiving a securing element, a clamping portion at the other end of the transfer part for the clamping connection of the transfer part to an implant, said clamping connection providing the sole connection between the transfer part and the implant, the clamping portion comprising a force transmission element for securing the clamping connection against rotation, a second radial groove directly adjacent to the force transmission element, and a clamp ring insertable into the second radial groove,
- wherein the dental implant comprises an internal undercut positioned correspondingly to the second radial groove of the clamping portion of the transfer part and dimensioned suitably to provide together with the second radial groove a receiving means for clampingly receiving the clamp ring, and
- wherein the inner ampule has an upper fixing portion which reaches to a large surface recess in the inner ampule for insertion and removal of the transfer part, wherein the upper fixing portion has a laterally open indentation enlarging radially towards the recess which is adapted for the closely fitting insertion of a portion of the transfer part, and a lower fixing portion adapted to receive the implant.

7. An inner ampule for receiving and securing a transfer part for a dental implant, with the inner ampule having an upper fixing portion which reaches to a large surface recess in the inner ampule for insertion and removal of the transfer part, wherein the upper fixing portion has a laterally open indentation towards the recess which is adapted for the closely fitting insertion of a portion of the transfer part, and a lower fixing portion also having a laterally open indentation towards the recess and adapted to receive the implant,
- wherein the transfer part comprises a free extension at one end of the transfer part for coupling a rotational tool and a first radial groove adjacent to the free extension for receiving a securing element, a clamping portion at the other end of the transfer part for the clamping connection of the transfer part to an implant, said clamping connection providing the sole connection between the transfer part and the implant, the clamping portion comprising a force transmission element for securing the clamping connection against rotation, a second radial groove directly adjacent to the force transmission element, and a clamp ring insertable into the second radial groove to engage with the dental implant, and
- wherein the dental implant includes an internal undercut positioned correspondingly to the second radial groove of the clamping portion of the transfer part and dimensioned suitably to provide together with the second radial groove a receiving means for clampingly receiving the clamp ring.

8. The inner ampule according to claim 7, where the indentation of the upper fixing portion enlarges radially toward the recess and where the lower fixing portion is configured in the form of two support wings.

9. The inner ampule according to claim 7, where the indentation is adapted to clampingly receive a fixing portion of a transfer part and where the lower fixing portion is adapted to receive an implant shoulder.

10. The inner ampule according to claim 7, where the recess is formed with rounded corners at its lower portion opposite to the indentation.

* * * * *